United States Patent [19]

Petrofsky et al.

[11] Patent Number: 4,556,214
[45] Date of Patent: * Dec. 3, 1985

[54] METHOD AND APPARATUS FOR EXERCISING

[75] Inventors: Jerrold S. Petrofsky, Beavercreek; Roger M. Glaser, Dayton; Steven H. Petrofsky; Harry H. Heaton, III, both of Beavercreek, all of Ohio

[73] Assignee: Wright State University, Dayton, Ohio

[*] Notice: The portion of the term of this patent subsequent to Nov. 6, 2001 has been disclaimed.

[21] Appl. No.: 644,167

[22] Filed: Aug. 24, 1984

Related U.S. Application Data

[63] Continuation of Ser. No. 417,935, Sep. 14, 1982, Pat. No. 4,480,830.

[51] Int. Cl.$^4$ .............................................. A63B 21/12
[52] U.S. Cl. .................................... 272/117; 272/134; 272/DIG. 5; 272/DIG. 6; 128/25 R; 128/795; 128/423 W
[58] Field of Search ............... 272/93, 117, DIG. 5, 272/DIG. 6; 128/423 W, 423 R, 733, 25 B, 25 R, 24.1, 796, 80 G, 80 R, 795, 363, 364

[56] References Cited

U.S. PATENT DOCUMENTS

| | | |
|---|---|---|
| 1,498,529 | 6/1924 | Allen . |
| 2,630,115 | 3/1953 | Bierman ................................. 128/44 |
| 2,815,020 | 12/1957 | Barkschat ............................. 128/25 |
| 3,000,632 | 9/1961 | Fuchs ..................................... 272/58 |
| 3,083,712 | 4/1963 | Keegan ................................ 128/423 |
| 3,204,637 | 9/1965 | Frank et al. ........................ 128/423 |
| 3,344,792 | 10/1967 | Offner et al. ....................... 128/419 |
| 3,387,147 | 6/1968 | Radwan .............................. 307/275 |
| 3,628,538 | 12/1971 | Vincent ............................... 118/422 |
| 3,817,254 | 6/1974 | Maurer ................................ 128/421 |
| 3,848,467 | 11/1974 | Flavell ................................... 73/379 |
| 3,911,910 | 10/1975 | Oesau ................................. 128/82.1 |
| 3,929,335 | 12/1975 | Malick ................................... 272/57 |
| 3,989,240 | 11/1976 | Victor et al. ........................ 272/125 |
| 4,071,033 | 1/1978 | Nawracaj et al. ................... 128/420 |
| 4,148,321 | 4/1979 | Wyss et al. .......................... 128/420 |
| 4,165,750 | 8/1979 | Aleev et al. .......................... 128/422 |
| 4,177,819 | 12/1979 | Kofsky et al. ....................... 128/422 |
| 4,236,528 | 12/1980 | Stanec et al. ........................ 128/741 |
| 4,257,590 | 3/1981 | Sullivan et al. ...................... 272/117 |
| 4,284,157 | 8/1981 | Lay ........................................ 180/65 |
| 4,333,340 | 6/1982 | Elmeskog ............................. 73/379 |
| 4,392,496 | 7/1983 | Stanton .............................. 128/423 |

FOREIGN PATENT DOCUMENTS

| | | |
|---|---|---|
| 2052994 | 2/1981 | United Kingdom . |
| 635995 | 5/1979 | U.S.S.R. . |
| 719635 | 8/1980 | U.S.S.R. . |

OTHER PUBLICATIONS

"Alteration in the Force and Fatigability of Skeletal Muscle in Quadriplegic Humans Following Exercise Induced by Chronic Electrical Stimulation", *Clinical Orthopaedics and Related Research* No. 114, Feb. 1976, pp. 326–334, by Peckham et al.

(List continued on next page.)

*Primary Examiner*—Richard C. Pinkham
*Assistant Examiner*—Leo P. Picard
*Attorney, Agent, or Firm*—Biebel, French & Nauman

[57] ABSTRACT

An exercising method and apparatus for use in the treatment of paralyzed muscles. The method and apparatus make use of a set of transcutaneous electrodes which are placed upon the skin of the subject over muscles which are to be stimulated. A computer controlled stimulator generates a pair of alternately pulsed stimulation signals which are applied across different pairs of stimulation electrodes to produce controlled muscle contraction. Muscle movement is resisted by a dynamic load, and a position sensor provides a feedback signal indicating the movement actually achieved. The computer uses the feedback signal for modifying the control signal applied to the stimulator. The exercise routine is disclosed as being conducted upon the leg of a subject seated in a specially designed exercise chair.

6 Claims, 8 Drawing Figures

OTHER PUBLICATIONS

Microprocessor Controlled Stimulation in Paralyzed Muscle, Petrofsky and Phillips, IEEE NAECON Record (Dec. 1979), pp. 198-210.

Muscle Fiber Recruitment and Blood Pressure Response to Isometric Exercise, Petrofsky et al., J. Appl. Physiol.: 50(1), pp. 32-37, Nov. 1981.

Control of the Recruitment and Firing Frequencies of Motor Units in Electrically Stimulated Muscles in the Cat, Med. & Biol. Eng. & Comput., 12/78, 16, pp. 302-308.

Sequential Motor Unit Stimulation through Peripheral Motor Nerves in the Cat, Petrofsky, Med. & Biol. Eng. & Comput., 11/79, pp. 087-093.

The Influence of Temperature, Initial Length and Electrical Activity on the Force-Velocity Relationship of the Medial Gastrocnemius Muscle of the Cat, Petrofsky and Phillips, J. Biomechanics, vol. 14, No. 5, pp. 397-306, Dec. 1981.

Constant-Velocity Contractions in Skeletal Muscle by Sequential Stimulation of Muscle Efferents, Petrofsky and Phillips, Med. & Biol. Eng. & Comput., Nov. 1979, 17, pp. 583-592.

Impact of Recruitment Order on Electrode Design for Neural Prosthesis of Skeletal Muscle, Petrofsky and Phillips, Am. J. Phys. Med., vol. 60, Nov. 1981, pp. 243-253.

New Microcomputer May Someday Bring Paralyzed Limbs to Life, Philips J. Hilts-Washington Post on Feb. 16, 1981.

Walking Away from Paralysis by Denise Grady, Discover Magazine, May 1981, pp. 26-28 and 30.

Control of Contraction Strength of Electrically Stimulated Muscle by Pulse Width and Frequency Modulation, Peckham, Proc. 29th ACEMB, p. 116, Nov. 6-10, 1976.

The Effects of Lengths and Stimulus Rate on Tension in the Isometric Cat Soleus Muscle, Rack & Westbury, J. Physiol. (Dec. 1969) 205, pp. 443-460.

Clinical Electrical Stimulation by G. Keith Stillwell (name of publication unknown), pp. 114-117.

METHOD AND APPARATUS FOR EXERCISING

CROSS REFERENCE TO RELATED APPLICATION

This application is a continuation of Ser. No. 417,935 filed Sept. 14, 1982, now U.S. Pat. No. 4,480,830.

BACKGROUND OF THE INVENTION

The present invention relates to a method and apparatus for exercising and, more particularly, to a computer controlled method and apparatus for monitoring muscular activity and adjusting an electrical stimulus to provide controlled and sustained isokinetic contractions. Still more particularly the present invention relates to a method and apparatus for directing coordinated movement of several muscles and exercising them through a specific exercise routine having therapeutic applications in the treatment of paralysis.

The invention which is disclosed and claimed herein has particular value in the treatment of persons who have suffered injuries resulting in spinal cord damage. This particular type of damage often times produces partial or total paralysis of muscles which are controlled from a point below the point of spinal cord damage. The victim then faces a life of relative inactivity and deterioration of muscles which otherwise would be active. It has now been found in accordance with this invention that such muscles can be stimulated to engage in an exercise program once thought to be impossible. Moreover, it has been found that such an exercise program can restore normal muscle tone, even after years of inactivity.

Since the work of Galvani in 1791, it has been known that electricity can be used to induce muscle contractions. Recently, there has been increased awareness of the value of electrostimulation in muscle therapy.

Numerous devices and techniques have been developed for supplying electrical pulses as part of a therapeutic regime of muscle stimulation. Several examples of these are found in the patent literature. Radwan, U.S. Pat. No. 3,387,147 (1968) discloses a muscle stimulating pulse generator designed to provide a pulse signal having a relatively high voltage-to-width ratio and a steep rising wavefront.

Maurer, U.S. Pat. No. 3,817,254 (1974), discloses a transcutaneous stimulator for use in suppressing pain designed to differentially stimulate touch versus pain nerve fibers in an effort to reduce the prickly sensation known to accompany some pain therapy. Maurer notes that differences in the response of nerves to electrostimulation can be used to selectively stimulate different types of nerves. According to Maurer, nerve fibers are distinguished in terms of their size and conduction velocity. He notes that the amplitude of electrical stimulation required to elicit a muscle response increases as the fiber size decreases.

Nawracaj et al, U.S. Pat. No. 4,071,033 (1978), discloses an electrostimulation device which utilizes a heterodyne effect to produce an otherwise painful low frequency stimulus in a muscle and cause the muscle to contract and relax at a low frequency.

Wyss et al, U.S. Pat. No. 4,148,321 (1979), discloses a muscular therapy similar in some respects to Nawracaj et al wherein muscles are made to rhythmically contract and relax at a very low frequency which is induced by modulating a medium frequency current between 3,000 and 100,000 Hz with a low frequency current less than 1 Hz. In one embodiment Wyss et al uses a phase shifter to transform the modulated output current into a three phase current, which is delivered to three electrodes angularly spaced about a limb to provide deep uniform stimulation.

Kofskey et al, U.S. Pat. No. 4,177,819 (1979), teaches an apparatus for stimulating a muscle for 2 to 20 seconds at 2 to 50 second intervals using a 2000 to 3000 Hz signal modulated at 40 to 50 Hz. In one embodiment, the muscle stimulating waveform is controlled by a microprocessor which gradually increases and decreases the amplitude of the stimulation at the beginning and end of each pulse. The microprocessor responds to signals from a no-load/overload sensor and to a manually controlled gain setting signal.

It can be seen that the efforts embodied in the foregoing patents focus on the stimulus itself as the therapeutic agent and have as a principal objective to optimize the intensity, duration and frequency of the stimulus to enhance its therapeutic effects. In the disclosed therapies, the muscle is not stimulated against a load. These prior art systems do not provide smooth isometric contractions and do not respond to muscle activity response to muscle activity in these prior systems.

In order to train a muscle and make it physically strong, it is necessary to work the muscle against a load while producing powerful, sustained, isokinetic contractions at a substantial proportion of the muscle's strength. Isokinetic contractions cannot be maintained for prolonged periods of time in the aforementioned therapies, because they stimulate the muscle synchronously using frequencies much higher than normal physiological frequencies. This causes the muscle to fatigue rapidly, making it impossible to maintain muscle tension.

Petrofsky, "Microprocessor Controlled Stimulation in Paralyzed Muscle", IEEE August 1979 outlines a computer-controlled stimulation system which mimics normal asynchronous recruitment of motor units and firing rate control in the gastrocnemius muscle of a cat. A computer was programmed to set the recruitment order of the motor units as it sensed fatigue in the muscle. This was accomplished by using an anodal block electrode in combination with a sequential electrode sleeve. The electrode sleeve was placed around the motor nerve to the muscle and was configured for alternately stimulating three groups of neurons in the nerve. The anodal block electrode was placed just proximal to the muscle. Muscle fatigue was sensed by a strain gauge transducer mounted on a bar attached to one end of the muscle.

The Petrofsky article teaches that electrostimulation can be controlled by a microprocessor in such a way as to develop isometric contractions in a muscle. However, there is no teaching of any method or apparatus for causing smooth, natural isokinetic contractions. Also, the techniques taught by Petrofsky are not applied to man.

SUMMARY OF THE INVENTION

It is an object of the present invention to provide a method and apparatus for electrically stimulating a muscle and exercising the muscle through a specific exercise routine based upon feedback control.

It is another object of this invention to provide apparatus and method for stimulating a human muscle to contract against a dynamic load.

It is still another object of the invention to provide improved apparatus and method for stimulating contraction of a human muscle.

These and other objects of the present invention are accomplished through use of a stimulation device which generates a pair of stimulation signals comprising alternately generated pulses of stimulation energy. The stimulation signals are applied across pairs of electrodes which are preferably adhered to the skin immediately above a muscle to be stimulated.

In the preferred embodiment the stimulation apparatus is controlled through a digital to analog converter by a digitally controlled microprocessor. The limb which is moved by the stimulated muscle is secured against a dynamic load which yieldingly resists movement of the muscle. A feedback sensor senses the movement actually achieved by the limb and transmits an indication thereof through an analog to digital converter back to the microprocessor.

In an exercise routine according to the present invention, a plurality of transcutaneous stimulators are applied to the skin of the subject in a pattern for stimulating a muscle which is connected for moving the limb to be exercised. The stimulators are then excited by a plurality of stimulation signals having profiles for causing the muscle to contract and produce a predetermined movement of the limb. While the limb is contracting, a resisting force is applied thereagainst to cause exertion of the muscle during its contraction. The movement of the limb is sensed and a corresponding feedback signal is generated. The feedback signal is monitored to determine when a predetermined movement has been achieved. After the predetermined movement has been achieved, the stimulation signals are altered to permit the limb to return to its initial position. The process is then repeated to produce an exercise routine.

DESCRIPTION OF THE PREFERRED EMBODIMENT

Figures 1, 2, 3:
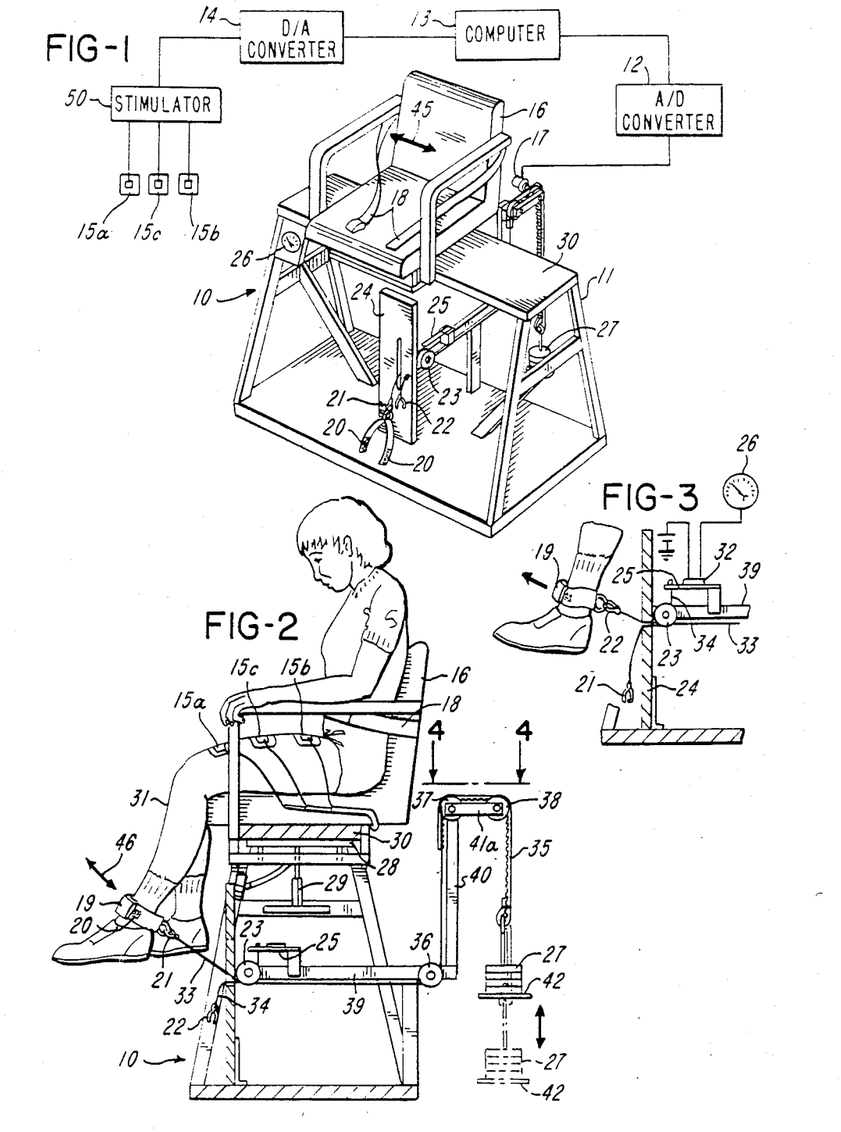
FIG. 1 is a schematic illustration of exercising apparatus in accordance with the present invention.
FIG. 2 is a side elevation view of an exercise chair.
FIG. 3 is an illustration of means for indicating the isometric load developed by a human leg.

FIG. 1 illustrates an exercise system 10 constructed in accordance with this invention. The exercise system may comprise a chair 16 mounted on a support frame 11. Chair 16 rests upon a support board 30 and is clamped in place by a clamp plate 28, as illustrated in FIG. 2. Clamp plate 28 may be forced upwardly against the lower surface of support board 30 by any convenient means, such as, for instance, a rotary handle and screw arrangement 29. When clamp 28 is released chair 16 may be moved along the surface of support board 30 as illustrated by the arrow 45. This enables positioning of chair 16 for accommodating an exercise routine for either the left leg or the right leg of a person seated in chair 16.

Exercise system 10 also comprises a seat belt 18 for securing a person in chair 16 and a leg strap 19 for grasping the lower portion of a leg 31. Leg strap 19 is provided with interlocking pieces of hook and loop fastening fabric 20, 20 of the type sold by Velcro U.S.A., Inc. of New York, N.Y. under the trademark VELCRO. Thus leg strap 19 be easily and securely fastened around a leg of any size.

Leg strap 19 has a steel eyelet for fastening to one or the other of a pair of scissor-type eyelet fasteners 21, 22. Fasteners 21 and 22 are attached to pair of cables 33, 34, respectively, which extend through a facing board 24.

Cables 33 and 34 are guided by a roller 23 having a pair of offset guide channels (not illustrated). Cable 33 extends rearwardly from roller 23 around a roller 36 and thence upwardly for attachment to a toothed belt 35. Cable 34 wraps around roller 23 and extends upwardly for attachment to a relatively stiff bending arm 25 supported upon frame member 39, as best illustrated in FIG. 3.

Figure 4:
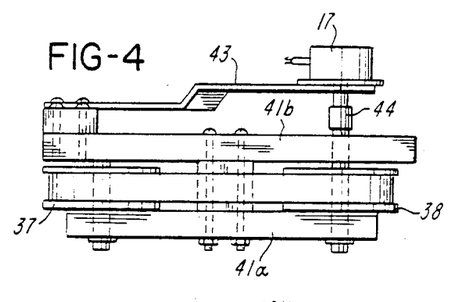
FIG. 4 is a view taken along line 4—4 of FIG. 2.

Toothed belt 35 extends around a pair of toothed rollers 37 and 38 mounted between a pair of support plates 41a and 41b, as best illustrated in FIG. 4. Support plates 41a and 41b are securely supported by frame member 40, which in turn is supported by frame member 39.

Belt 35 supports a set of weights placed upon a pan 42. Thus when the leg 31 moves arcuately as indicated by arrow 46, the weights 27 are raised or lowered. The arrangement provides a dynamic load which resists but does not prevent movement of leg 31.

When the leg 31 is extended upwardly, pulling cable 33 and belt 35, the movement is measured by a potentiometer 17 (see FIG. 4) attached to roller 38 by a coupling device 44. The housing for potentiometer 17 is supported by a support arm 43 secured to the upper support plate 41, as viewed in FIG. 4.

As the leg 31 moves and pulls belt 35 across roller 38, the potentiometer 17 transmits a feedback signal to A/D converter 12. A/D converter 12 converts the feedback signal into a digital format for processing by computer 13, as hereinafter described in detail. Computer 13 responds to the feedback signal by transmitting a digital control signal to D/A converter 14. D/A converter 14 then generates an analog stimulation signal for stimulator 50. Stimulator 50 uses the control signal from D/A converter 14 for generation of a pair of stimulation signals which are applied across electrodes 15a, 15b and 15c. Electrodes 15a, 15b and 15c are commercially available transcutaneous electrodes such as MEDTRONIC Model 3793 electrodes sold by Medtronic, Inc. of Minneapolis, Minn.

For an exercise as hereinafter described the electrodes are placed in spaced positions above the quadriceps muscles of one leg, as generally illustrated in FIG. 2. The electrodes are attached to the leg of the subject by hypoallergenic tape or elastic bandages. Prior to application of the electrodes, the skin is cleaned and dried. An electrode gel, such as TENS electrode gel, also sold by Medtronic, Inc. is applied to the electrodes before they are placed upon the skin of the subject.

When the stimulation signals from stimulator 50 are applied to electrodes 15a, 15b and 15c the quadriceps muscles of the subject are stimulated to contract and raise the leg 31 against the dynamic resistance of cable 33 as described above. Alternatively, leg strap 19 may be connected to cable 34 in which case leg 31 strains isometrically against bending arm 25. This produces an output signal from a strain gauge 32 mounted on top of bending arm 25. Strain gauge 32 is connected to provide a load signal for a meter 26 which may be mounted at any convenient location. The meter 26 provides a "strength" indication for use in the exercise procedure hereinafter described in detail.

Figure 7:
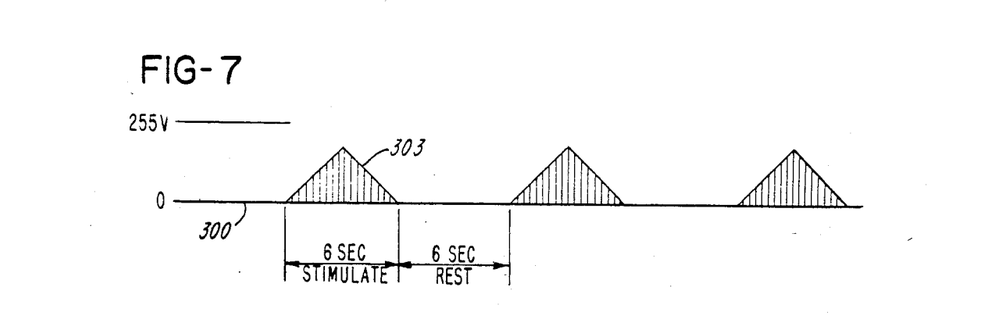
FIG. 7 is a schematic illustration of a stimulation signal.
Figure 8:
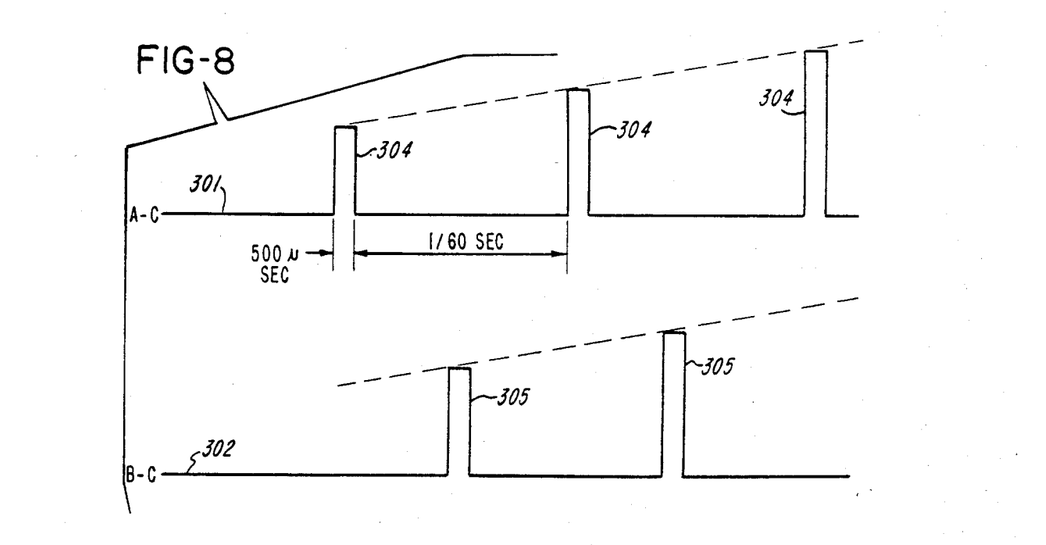
FIG. 8 is an enlarged schematic illustration of portions of two alternately pulsed stimulation signals.

The stimulation signals which are applied to electrodes 15a, 15b, and 15c are illustrated in FIGS. 7 and 8. Stimulator 50 generates a first signal 301 as illustrated by the top line of FIG. 8 and a second signal 302 as illustrated by the bottom line of FIG. 8. Signal 301 is applied across terminals 15a and 15c, while signal 302 is applied terminals 15b and 15c. Terminal 15c is connected to high voltage ground, as hereinafter described with reference to FIG. 5.

Each of signals 301 and 302 has an envelope generally illustrated by triangular projections 303 rising above the line 300 of FIG. 7. The signal is characterized by alternating stimulation and rest periods of approximately 6 seconds each. During the stimulation period the signal is pulsed at a frequency in a range from about 55 to 65 Hz and preferably about 60 Hz. The pulses which are so generated have peak values which increase gradually from a value near 0 volts to a maximum which is somewhat less than 255 volts and which produces maximum effort from the muscle or muscle group being stimulated. Thereafter the pulse amplitudes decrease gradually to a value near zero, and the muscle is rested. The maximum voltage value depends upon the state of exhaustion of the muscle and the effort which is desired. As the muscle tires, more stimulation voltage is required for production of the same effort. Generally speaking a maximum voltage of about 255 volts produces recruitment of all motor units and results in maximum effort by the muscle.

As shown in FIG. 8, signal 301 comprises a series of pulses 304 while signal 302 comprises another series of pulses 305. Pulses 304 and 305 are generated in an alternating sequence at a frequency of 60 Hz each. Thus the effective combined frequency is 120 Hz. Pulses 304 and 305 have peak values which conform with the signal envelope of FIG. 7. They have a duration of approximately 500 microseconds, so that each of signals 301 and 302 has a duty cycle of 0.03. It has been found that if the pulse width is increased, then the stimulation voltage may be decreased and vice versa.

Figure 5:
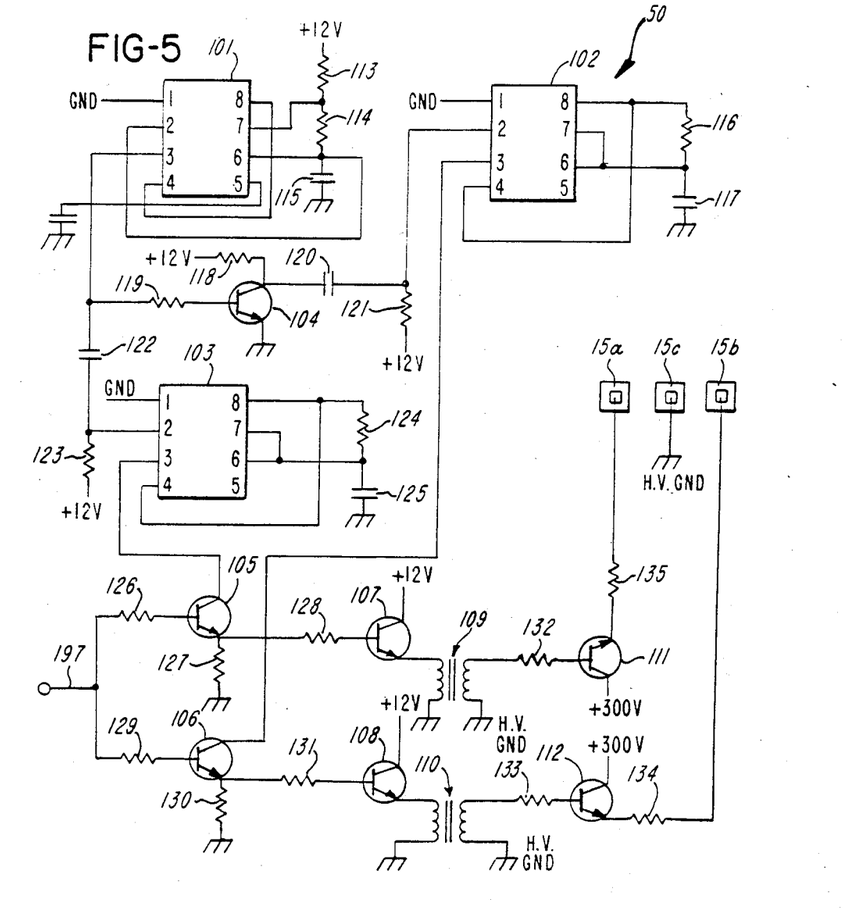
FIG. 5 is a schematic illustration of a stimulation apparatus.

The circuitry for producing signals 301 and 302 is illustrated in FIG. 5. The associated feedback and control circuitry is illustrated schematically in FIG. 6. The circuitry includes integrated circuits as identified in Table I and components as identified in Table II. Table III lists significant pin number designations for the principal integrated circuits listed in Table I.

TABLE I

| Ref. Numeral | Integrated Circuits Circuit Type |
|---|---|
| 12 | ADC0808 (National Semiconductor) |
| 13 | DAC0831 (National Semiconductor) |
| 101 | SE/NE 555 (Signetics) |
| 102 | SE/NE 555 (Signetics) |
| 103 | SE/NE 555 (Signetics) |
| 201 | SN74LS138 (Texas Instruments) |
| 204 | SE/NE 555 (Signetics) |
| 205 | 1/6 7404 |
| 206 | ¼LM1458 |
| 207 | 1/6 7404 |
| 208 | 1/6 7404 |
| 209 | ¼LM1458 |
| 210 | ¼LM1458 |
| 211 | ¼LM1458 |
| 212 | ¼LM1458 |
| 213 | ¼LM1458 |
| 214 | ¼LM1458 |

TABLE II

| Ref. Numeral | Components Identification |
|---|---|
| 104 | 2N3904 |
| 105 | 2N3904 |
| 106 | 2N3904 |
| 107 | 2N3904 |
| 108 | 2N3904 |
| 111 | 2SC1308 |
| 112 | 2SC1308 |
| 113 | 100k |
| 114 | 100k |
| 115 | $0.1\mu f$ |
| 116 | 10k |
| 117 | $0.1\mu f$ |
| 118 | 10k |
| 119 | 10k |
| 120 | $0.001\mu f$ |
| 121 | 22k |
| 122 | $0.001\mu f$ |
| 123 | 22k |
| 124 | 10k |
| 125 | $0.1\mu f$ |
| 126 | 470Ω |
| 127 | 10k |
| 128 | 470Ω |
| 129 | 470Ω |
| 130 | 10k |
| 131 | 470Ω |
| 132 | 1k |
| 133 | 1k |
| 134 | 100Ω |
| 135 | 100Ω |
| 136 | $0.1\mu f$ |
| 219 | $39\mu f$ |
| 220 | $10\mu f$ |
| 221 | 100k |
| 222 | 330k |
| 223 | 680k |
| 234 | 100k |
| 235 | 82k |

TABLE III

| Component | Pin No | Pin Functions Function Name | Function |
|---|---|---|---|
| Slot #3 of Apple Computer | 1 | I/O SELECT | LO during slot #3 addressing |
| | 2 | A0 | Address bit 0 |
| | 3 | A1 | Address bit 1 |
| | 4 | A2 | Address bit 2 |
| | 7 | A5 | Address bit 5 |
| | 8 | A6 | Address |
| | 9 | A7 | Address bit 7 |
| | 18 | R/W | Buffered Read/Write signal |
| | 25 | +5V | +5 volts |
| | 26 | GND | ground |
| | 33 | -12v | -12 volts |
| | 40 | 0 | phase 0 clock |
| | 42 | D7 | Data bit 7 |
| | 43 | D6 | Data bit 6 |
| | 44 | D5 | Data bit 5 |
| | 45 | D4 | Data bit 4 |
| | 46 | D3 | Data bit 3 |
| | 47 | D2 | Data bit 2 |
| | 48 | D1 | Data bit 1 |
| | 49 | D0 | Data bit 0 |

TABLE III-continued

| Component | Pin No | Pin Functions Function Name | Function |
|---|---|---|---|
| | 50 | +12v | +12 volts |
| SN74LS138 | 1 | A | select line |
| | 2 | B | select line |
| | 3 | C | select line |
| | 4 | G2A | enable line |
| | 5 | G2B | enable line |
| | 6 | G1 | enable line |
| | 10 | Y5 | output line |
| | 12 | Y3 | output line |
| | 14 | Y1 | output line |
| ADC 0808 | 3 | In5 | analog input #5 |
| | 6 | start | start strobe |
| | 8 | D3 | Data bit 3 |
| | 9 | out enable | output enable |
| | 10 | clock | clock |
| | 14 | D1 | data bit 1 |
| | 15 | D2 | data bit 2 |
| | 17 | D0 | data bit 0 |
| WSU 013A P2 | 18 | D4 | data bit 4 |
| | 19 | D5 | data bit 5 |
| | 20 | D6 | data bit 6 |
| | 21 | D7 | data bit 7 |
| | 23 | Add C | address bit C |
| | 24 | Add B | address bit B |
| | 25 | Add A | Address bit A |
| | 27 | In 1 | analog input #1 |
| | 28 | In 2 | analog input #2 |
| DAC 0831 | 1 | CS | input latch |
| | 2 | WR1 | data load |
| | 4 | $DI_3$ | digital input bit 3 |
| | 5 | $DI_2$ | digital input bit 2 |
| | 6 | $DI_1$ | digital input bit 1 |
| | 7 | $DI_0$ | digital input bit 0 |
| | 9 | $R_{fb}$ | zero adjustment |
| | 11 | $I_{out\ 1}$ | output proportional to digital input |
| | 12 | $I_{out\ 2}$ | output proportional to complement of digital input |
| | 13 | $DI_7$ | digital input bit 7 |
| | 14 | $DI_6$ | digital input bit 6 |
| | 15 | $DI_5$ | digital input bit 5 |
| | 16 | $DI_4$ | digital input bit 4 |
| | 19 | $I_{LE}$ | chip select |

The operation of stimulator 50 will now be described with reference to FIG. 5. That figure shows 3 integrated circuits 101, 102, and 103 of identical construction. These are timing circuits such as Signetics 555 timers. IC 101 is connected to operate as a 60 Hz free running multivibrator. The output from IC 101 is applied via transistor 104 to input pins 2 of IC 102 and 103. IC 102 and 103 produce alternating 500 microsecond pulses each at a frequency of 60 Hz for application to the collector terminals of transistors 105 and 106. The pulse width is set by appropriate selection of the resistance for resistors R116 and R124 and the capacitance of capacitors 117 and 125, as shown in the manufacturer's data sheets for integrated circuits 102 and 103. The phase between the pulses produced by integrated circuits 102 and 103 is set by appropriate selection of the resistance for resistors 113 and 114.

An analog voltage representing the desired envelope for the stimulation pulses is applied to input line 197, which is connected to the base terminals of transistors 105 and 106. Concomitantly, output pulses from pin 3 of IC 102 and pin 3 of IC 103 are applied to the collectors of transistors 106 and 105 respectively. As a result thereof transistors 106 and 105 generate emitter currents across resistors 130 and 127 providing voltage profiles of the general shape illustrated in FIGS. 7 and 8. These voltages are applied to the base terminals of transistors 108 and 107. This results in corresponding voltage pulses ranging between 0 and 12 volts across the primary windings of transformers 110 and 109.

The voltage pulses across the primary windings of transformers 110 and 109 produce low current, high voltage pulses ranging from 0 to 255 volts across the secondary windings of transformers 110 and 109. The secondary windings of transformers 110 and 109 have one side grounded to a high voltage ground which is different from the ground utilized for the primary windings thereof. The output pulses from the secondary windings are thereby RF isolated to maintain the safety of the person who is the subject of the exercise procedure.

Figure 6:
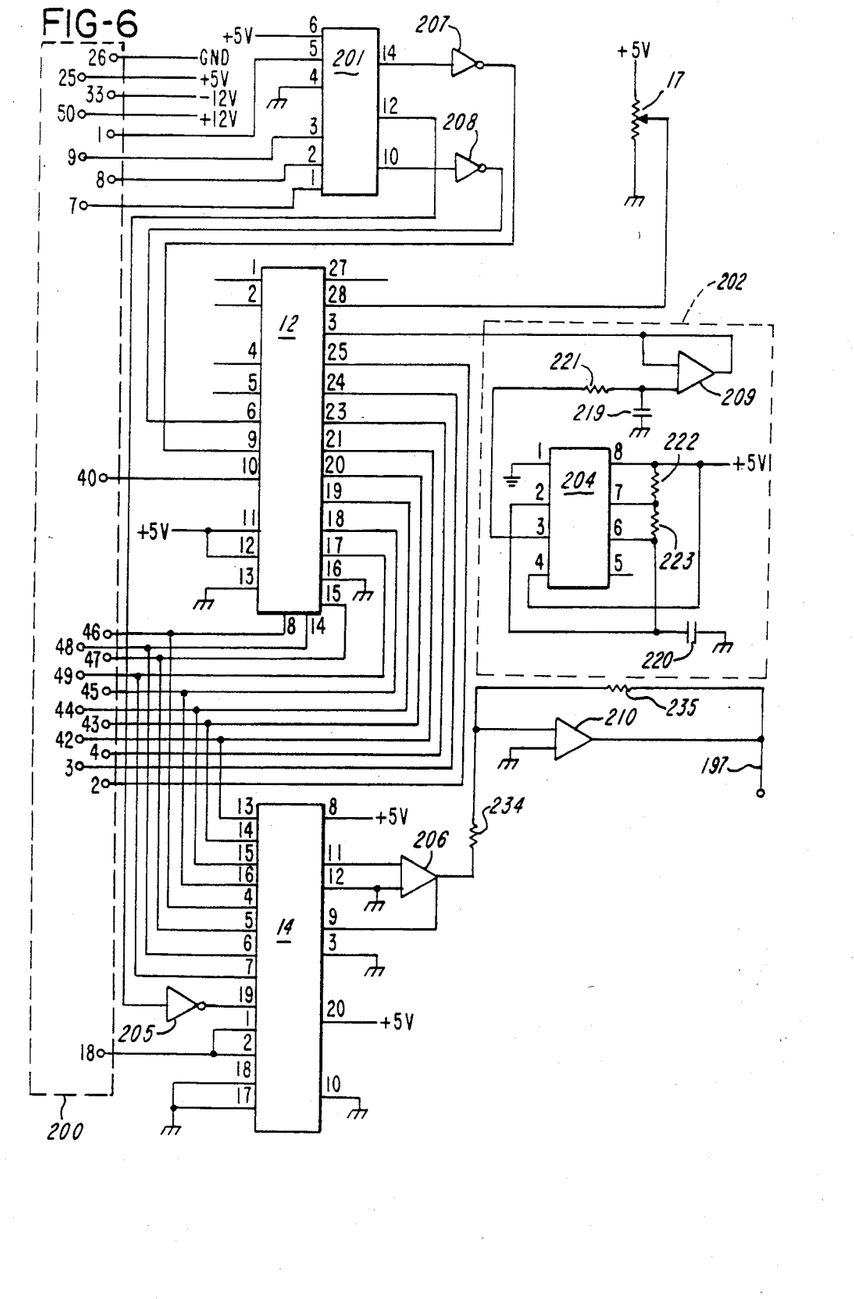
FIG. 6 is a schematic illustration of a control system for the stimulation apparatus of FIG. 5.

Output voltage pulses from transformers 110 and 109 are applied to the base terminals of transistors 112 and 111 respectively. Transistors 112 and 111 provide a current gain so as to have high current, high voltage and low duty cycle pulses available for application across terminal pairs 15a-15c and 15b-15c. The analog driving signal appearing at line 197 is generated by the control system circuitry as illustrated in FIG. 6.

The heart of the control system is the computer 13, which in the embodiment described herein is an APPLE II computer sold by Apple Computer Inc. of Cupertino, Calif. The APPLE II computer is provided with several slots into which may be plugged connectors for customized peripheral devices. The system described herein is plugged into slot number 3, which includes a connector 200 as illustrated by dotted lines in FIG. 6. The computer addresses analog to digital converter 12 and digital to analog computer 13 through a decoder/demultiplexer 201. The peripheral board is addressed by the computer in memory locations C100 to C1FF (hexadecimal notation). Pin number 1 of connector 200 provides a signal from the computer's input/output select line. This line becomes active whenever one of the memory locations C1FF to C100 are selected for memory read or write operations. Pin number 1 is tied to pin number 5 of IC 201, an SN74LS138 integrated circuit. Pin number 5 is the G2 input of IC 201. A signal at this terminal enables IC 201 to decode the three high order bits (A7, A6, and A5) of an eight-bit address provided by the computer. These three bits appear at pin numbers 9, 8 and 7 respectively of connector 200.

IC 201 is designed for producing eight decoded outputs, but only three of these outputs are used. These outputs appear at pin members 14, 12 and 10 and respectively read A/D converter 12, strobe D/A converter 14 and strobe A/D converter 12. A/D converter 12 is an eight channel device sold by National Semiconductor under the designation ADC0808. A/D converter 12 receives its clock from the system clock on pin number 40 of connector 200.

When a strobe signal appears at pin number 12 of IC 201, A/D converter 12 is enabled for reading and digitizing analog signals appearing at any one of eight analog input ports (only two of which are used). The two analog input ports are addressed by a three-bit address appearing at pin numbers 25, 24 and 23 of A/D converter 12. The three address bits are the three least significant bits of an eight-bit address generated by computer 13. These three bits appear at pin members 2, 3 and 4 of connector 200 (the three most significant bits appearing at pin numbers 7, 8 and 9 as above stated and bit numbers 3 and 4 not being utilized.

Computer 13 generates the above mentioned eight-bit address whenever any one of computer memory address locations 50080 to 50087 (decimal notation) are strobed. Such strobing not only generates an associated eight-bit address, but also enables A/D converter 12 by causing generation of a strobe signal at output pin 12 of IC201, as above described. Memory locations 50080 to 50087 are strobed by execution of a "POKE" instruction, such as, for instance, the instruction "POKE 50080,0" appearing at line number 1450 of the computer program set forth in TABLE IV hereof.

TABLE IV

```
1        POKE 50016,10
2        REM Z=THRESHOLD VOLTAGE
3        REM STRENGTH=MAXIMUM VOLTAGE LEVEL
4        REM K3=LOW GAIN CAL...K2 =HIGH GAIN CAL
5        REM G3=REAL STRENGTH
6        K3 = .05:K2 = 1 / 46
7        DIM A(1000)
10       REM ********************************
20       REM EXERCISE 1 PROGRAMS
30       REM ********************************
40       REM
50       REM
51       POKE 50016,10
100      FOR X = 1 TO 30: PRINT : NEXT X
110      PRINT "THIS PROGRAM STIMULATES": PRINT "  THE
         QUADRICEPS MUSCLE"
120      PRINT : PRINT : PRINT
125      PRINT "SET UP DYNAMOMETER FOR ISOMETRICS":
PRINT : PRINT
130      PRINT "CONNECT LEADS TO SUBJECT NOW"
140      PRINT : PRINT "BLACK LEAD TO CENTER"
150      PRINT
160      PRINT "TYPE GO OR WHEN READY"
170      INPUT A$
180      IF A$ = "GO" THEN 200
190      GOTO 160
200      PRINT : PRINT : PRINT : PRINT : PRINT :
         PRINT : PRINT
210      FOR I = 1 TO 25: PRINT : NEXT I
220      PRINT "MEASUREMENT OF ISOMETRIC STRENGTH"
230      PRINT : PRINT : PRINT : PRINT
240      PRINT "DEFINE THRESHOLD": PRINT
250      PRINT "   TO DETERMINE THE THRESHOLD": PRINT
         "WATCH THE MUSCLE AND NOTE": PRINT "WHEN THE
         MUSCLE STARTS TO ": PRINT "CONTRACT"
260      PRINT "TYPE ESC WHEN THE MUSCLE DEVELOPS":
         PRINT "TENSION"
270      PRINT : PRINT "THRESHOLD WILL BE PRINTED":
         PRINT "AT THE END"
271      PRINT : PRINT "SET DYNAMOMETER TO ZERO":
         PRINT "TURN ON STIMULATOR"
275      PRINT : PRINT : FLASH : PRINT "    CONTROL C
         TO STOP AND SWITCH": NORMAL
```

```
280     PRINT : PRINT "TYPE ANY KEY TO START": INPUT
        S$
283     PRINT : PRINT : FLASH
284     NORMAL
285     FOR H = 1 TO 300:U = SIN (H): NEXT H
290     FOR Y = 1 TO 17
295     PRINT "VOLTAGE LEVEL=";Y * 10
300     FOR I = 1 TO 150
310     POKE 50016,Y * 10
320     NEXT I
325     POKE 50016,10: FOR H = 1 TO 300: NEXT H
329     G1 = PEEK (49152): IF G1 = 155 THEN GOTO 400
330     NEXT Y
400     Z = Y * 10 - 10: PRINT : PRINT "THRESHOLD WAS
        ";Y * 10
401     POKE 49168,0
410     FOR X = 1 TO 1000: NEXT X
411     FOR X = 1 TO 3000: NEXT X
500     FOR H = 1 TO 700: NEXT H
550     FOR I = 1 TO 30: PRINT : NEXT I
599     INVERSE : PRINT "ISOKINETIC EXERCISE"
600     REM
601     NORMAL
610     FOR I = 1 TO 10: PRINT : NEXT I
620     FOR I = 1 TO 700: NEXT I
621     FOR I = 1 TO 2000: NEXT I
699     GOTO 1000: REM *****RE ACTIVATE FOR VARIABLE
        SPEED CONTRACTIONS BY REMOVING THIS
        LINE******************
700     PRINT "WHAT VELOCITY DO YOU WANT"
710     PRINT : PRINT : PRINT
720     PRINT "ENTER S FOR SLOW AND F FOR FAST":
        PRINT : PRINT : PRINT
730     INPUT D$
740     IF D$ = "S" THEN GOTO 800
750     IF D$ = "F" THEN GOTO 900
760     PRINT "NON LEGAL INPUT ....TRY AGAIN": GOTO
710
800     REM START SLOW ROUTINES
805     R = 3
810     LET VEL = R
850     GOTO 1000
900     REM START FAST ROUTINES
905     R = 50
910     LET VEL = R
950     GOTO 1000
1000    REM MAIN CONTROL PROGRAM
1010    POKE 50016,10
1020    REM DETERMINE STRENGTH
1030    FOR I = 1 TO 10: PRINT : NEXT I
1040    PRINT "DETERMINE MAXIMUM STRENGTH OF MUSCLE":
        PRINT : PRINT : PRINT
1041    PRINT "WHEN STRENGTH HAS LEVELED OFF": PRINT
        "TYPE ESC": PRINT : PRINT : FLASH : PRINT
        "CONTROL C AND SWITCH TO STOP FAST": NORMAL :
        PRINT
```

```
1043    PRINT : PRINT "TYPE GO TO START": INPUT A$:
        IF A$ = "GO" THEN GOTO 1044: GOTO 1043
1044    REM
1045    FOR J = Z TO 255 STEP 10
1046    PRINT "VOLTAGE LEVEL =";J
1050    FOR I = 1 TO 100
1060    POKE 50016,J
1070    REM
1080    NEXT I
1090    POKE 50016,10
1100    FOR U = 1 TO 2000: NEXT U
1105    G1 = PEEK (49152): IF G1 = 155 THEN GOTO 1120
1110    NEXT J
1120    PRINT : PRINT : PRINT "VOLTAGE LEVEL AT
        MVC=";J: PRINT : PRINT
1121    POKE 49168,0
1130    STRENGTH = J
1140    REM STRENGTH = VOLTAGE LEVEL AT MVC
1145    POKE 49168,0
1146    PRINT "WHAT IS THE READING?": INPUT METER:
        PRINT "INPUT THE GAIN...1 FOR HIGH.....2 FOR
        LOW": INPUT GAIN
1147    REM
1148    GOTO 8000
1149    FOR I = 1 TO 10: PRINT : NEXT I: GOSUB 5000
1150    FOR I = 1 TO 30: PRINT : NEXT I
1155    FOR I = 1 TO 30: PRINT : NEXT I
1156    D$ = ""
1157    PRINT D$; "RUN STIM"
1160    PRINT "SET UP DYNAMOMETER FOR DYNAMIC"
1170    PRINT "EXERCISE"
1180    NORMAL
1190    FOR I = 1 TO 10: PRINT : NEXT I
1200    REM
1220    PRINT "TYPE GO TO CONTINUE"
1230    INPUT A$
1240    IF A$ = "GO" THEN GOTO 1250: GOTO 1220
1250    REM   LOOK FOR START OF CYCLE
1255    D9 = 0
1260    FOR X = 1 TO 1000
1265    POKE 50080,0
1270    A(X) = PEEK (49952)
1280    NEXT X
1290    G7 = 150
1300    FOR X = 1 TO 1000
1310    IF G7 > A(X) THEN G7 = A(X)
1320    NEXT X
1330    POKE 50080,0
1340    G8 = PEEK (49952)
1350    IF G8 < G7 + 5 THEN GOTO 1400
1360    GOTO 1330
1400    REM STIMULATE THE LEG
1405    FLASH : PRINT "TURN OFF POWER THEN CONTROL C
        TO END": NORMAL
1410    PRINT "CONTRACTION ";D9 + 1:D9 = D9 + 1
1420    REM
```

```
1430    FOR X = 1 TO 250: NEXT X
1432    REM ********STIMULATE MUSCLE*****
1435    Z9 = Z
1440    POKE 50016,Z9
1441    IF Z9 = 255 THEN GOTO 6000
1450    POKE 50080,0:A8 = PEEK (49952): POKE
        50082,0:A9 = PEEK (49952)
1460    IF A8 > A9 THEN     LET Z9 = Z9 + 1
1470    IF A8 < A9 THEN     LET Z9 = Z9 -1
1480    IF A8 < G7 + 3 THEN GOTO 1500
1490    GOTO 1440
1500    POKE 50016,2
1510    FOR I = 1 TO 1000: NEXT I
1520    GOTO 1330
1530    REM
1540    REM
1550    REM
5000    REM *************************
5010    REM THIS SUBROUTINE LISTS STRENGTH AND LOAD
5020    REM ***********************
5030    REM
5040    PRINT : PRINT "WHAT TYPE OF EXPERIMENT?"
5041    PRINT "           1) FOR NO LOAD"
5042    PRINT "           2) FOR 33% LOAD"
5043    PRINT"           3) FOR 66% LOAD"
5044    PRINT
5050    INPUT TYPE
5055    IF TYPE > 4 THEN GOTO 5040
5056    IF TYPE = 0 THEN GOTO 5040
5057    IF TYPE = 4 THEN GOTO 5040
5060    IF GAIN = 1 THEN GOTO 5100
5070    IF GAIN = 2 THEN GOTO 5200
5080    GOTO 1145
5100    G3 = K2 * METER
5110    GOTO 5500
5200    G3 = K3 * METER
5210    GOTO 5500
5500    PRINT "THE STRENGTH WAS ";G3;" POUNDS"
5510    PRINT
5520    IF TYPE = 1 THEN GOTO 5600
5530    IF TYPE = 2 THEN GOTO 5700
5540    IF TYPE = 3 THEN GOTO 5800
5550    GOTO 1145
5600    PRINT "SET THE LOAD TO NO WEIGHT...": PRINT :
        PRINT "THIS IS A ZERO LOAD EXPERIMENT"
5610    GOTO 5900
5700    PRINT "THE LOAD MUST BE SET AT ";G3 / 3;" LBS"
5710    GOTO 5900
5800    PRINT "THE LOAD MUST BE SET AT ";2 * G3 /3;"
        LBS": PRINT : PRINT : PRINT: PRINT : FLASH :
        PRINT "SO......SET IT": NORMAL
5810    GOTO 5900
5900    FOR I = 1 TO 300:H = SIN (54): NEXT I
5910    RETURN
6000    REM *END PROGRAM DUE TO FATIGUE*
6005    POKE 50016,2
6010    PRINT : PRINT : PRINT : PRINT : PRINT : PRINT
```

```
6020    PRINT "THE MUSCLE IS BEING STIMULATED FULLY":
        PRINT "EITHER THE MUSCLE IS FATIGUED OR ":
        PRINT "SOMETHING IS WRONG...END PROGRAM"
6025    PRINT "TYPE " CONT " TO RESUME OR THE PROGRAM
        ENDS"
6026    INPUT A$: IF A$ = "CONT" THEN GOTO 1330
6030    END
8000    REM CHECK FOR BAD ENTRY
8010    IF METER = 0 THEN GOTO 1146
8020    IF METER > 1000 THEN GOTO 1146
8030    IF GAIN = 0 THEN GOTO 1146
8040    IF GAIN > 2.1 THEN GOTO 1146
8050    GOTO 1149
```

As mentioned above, the described embodiment supplies only two analog input signals for digitizing by A/D converter 12. These two signals appear at pin numbers 3 and 28 of A/D converter 12 and are addressed respectively by "POKING" memory locations 50080 and 50082 respectively. The resulting digitized representation thereof appears in eight-bit format at pin numbers 17, 14, 15, 8, 18, 19, 20 and 21 of A/D converter 12. These eight bits are read into memory location 49952 (decimal notation) upon execution of a "PEEK" instruction.

It is therefore seen that when memory addresses 50080 through 50087 are strobed, the computer selects the analog channel which is to be multiplexed into A/D converter 12. Simultaneously with this selection A/D converter 12 is strobed to start conversion of the analog signal to digital format. A maximum of 100 microseconds is required for the analog to digital conversion, after which the computer may execute a normal memory read cycle, whereby the digitized data is transferred onto the data bus and stored in memory location 49952. It is to be noted that the output of A/D converter 12 is an eight-bit binary signal ranging between values of 0 and 255 (decimal) for analog input voltages between 0 and 5 volts.

The analog signal supplied to pin No. 3 of A/D converter 12 has a triangular voltage profile and is produced by a profile generating circuit 202, comprising IC 204, amplifier 209, capacitors 219 and 220, and resistors 219 through 223. IC 204 generates a square wave at 1/6 Hz which is converted to a triangular ramp by capacitor 219 and resistor 221 and is buffered by amplifier 209. The triangular voltage profile, so generated, represents a desired response from potentiometer 17 when the leg of the subject is being stimulated to raise and lower.

The output of potentiometer 17 is applied to pin No. 28 of A/D converter 12, as shown in FIG. 6. An output of 5 volts from potentiometer 17 represents a shaft angle rotation of 360°. The diameter of roller 38 is selected such that one rotation thereof corresponds to a leg movement of about 70 degrees from its initial vertial position.

The amplitude of the analog stimulation signal appearing at line 197 is controlled by D/A converter 14, a DAC0831 integrated circuit sold by National Semiconductor. D/A converter 14 is selected for operation by applying a strobe signal to pin 19 thereof. Also, a write signal (logic L0) is applied to input terminals 1 and 2 for activating the transfer of data to the internal latch register of D/A converter 14. The data so transferred is an eight-bit stimulation command code appearing at terminals 13, 14, 15, 16, 4, 5, 6 and 7 of D/A converter 13. The output of D/A converter 14 is buffered and amplified and thereafter applied to input line 197 of stimulator 50.

Computer 13 generates eight-bit binary representation of stimulation command voltages ranging between 0 and 255 by executing an appropriate POKE instruction. A desired stimulation voltage ranging between 0 and 255 is POKED into memory location 50016 (decimal). When this memory location is POKED the computer generates an address for IC201 which causes output pin 12 to go L0. This L0 output signal is inverted by inverter 205 to create the above mentioned strobe signal for D/A converter 14.

The computer program for producing the above described operation is described in the program listing set forth in TABLE IV. This program is written in source code in accordance with the APPLESOFT variation of the well known BASIC language. The program will be self-explanatory to persons skilled in the art and only brief comments need be made.

The program set forth in TABLE IV includes an isometric strength measurement routine beginning at line 220 and a main control program beginning at line 1000. The main control program includes a start cycle beginning at line 1250 and a muscle stimulation routine beginning at line 1432. The start cycle finds the beginning of a ramp generated by the profile generator 202.

During the isometric measurement routine the computer increments a variable Y from 1 to 17 (line 290) and POKES the value 10Y into memory location 55016. This causes generation of stimulation pulses having a voltage equal to the value 10Y. When the muscle begins to develop tension, then the test supervisor depresses the Escape key on the computer control board. This action loads the ASCII code 155 into memory location 49152. The computer checks that memory location at line 329 and jumps to line 400 if the Escape key has been depressed. The computer then assigns the current value of 10Y to the variable Z as a threshold voltage.

After the threshold voltage has been established, the computer enters the main control program to determine the maximum strength of the muscle by isokinetic exercise. During this routine the computer steps the stimulation voltage from the value Z up to 255 volts in 10 volt steps (lines 1045 and 1060). During this period of time the leg is attached to cable 34 as indicated by FIG. 3. When strength meter 36 indicates that the strength has leveled off, then the test supervisor again depresses the Escape key. The computer checks memory location 49152 once during each voltage step (line 1105) and proceeds to line 1120, if the Escape key has been depressed.

After the maximum strength has been determined, the computer looks for a start of a cycle (line 1250).

The isokinetic exercise routine begins at line 1432. During this routine the computer generates stepped variations for a variable Z9 and POKES the value of Z9 memory location 50016. After each new value of Z9 has been utilized for generation of a corresponding stimulation voltage, the computer checks to see if Z9 has a value equal to 255 (maximum stimulation voltage). If that value is noted, than the isokinetic exercise routine is terminated. If not, the computer proceeds to execute the instructions at line 1450 which cause reading of the analog voltages generated by profile generator 202 and potentiometer 17. These voltages are digitized and utilized to establish values for variables A8 and A9 respectively.

If A8 is greater than A9, the computer knows that the leg is not raised as much as it should be, and the value of Z9 is increased. This then increases the stimulation voltage command generated by the computer. Conversely, if A8 is less than A9, Z9 and the stimulation command are decreased. When A8 has decreased to a value indicating the end of a cycle, then the leg is rested for the duration of a counting loop which continues for approximately 6 seconds.

A complete exercise procedure is therefore seen to include the following steps:

(1) Apply electrodes to subject.
(2) Turn on computer 13.
(3) Hook leg strap 19 to strength testing cable 34.
(4) Secure leg strap 19 to leg of subject.
(5) Connect electrical lead to electrode 15a, 15b and 15c with the HV ground line being connected to electrode 15c.
(6) Input "GO" into computer, thereby causing the computer to generate signals for application of stimulation voltages to electrode pairs 15a–15c and 15b–15c; the steps being in 10 volt increments from 10 volts to 170 volts max.
(7) Look for muscle contraction. When muscle contraction is noted, depress Escape key on computer, thereby causing the computer to store the threshold voltage.
(8) Determine muscle strength by typing "GO", into computer, thereby causing the computer to generate commands for production of stimulation voltages in 10 volt steps from the threshold voltage to a maximum of 255 volts.
(9) Observe strength meter. When strength has leveled off, depress Escape key on computer keyboard, thereby discontinuing the application of stimulation signals to the subject.
(10) Attach leg strap 19 to dynamic exercise cable 33.
(11) Place weights 27 on weight pan 42. The weight of the load should be some predetermined fraction of the maximum strength as determined above, typically one-third or two-thirds.
(12) Initiate isokinetic exercise by typing "GO" into computer. This command causes generation of a stimulation voltage profile as illustrated in FIGS. 7 and 8. The leg reacts to this voltage profile by repeated cycles of raising, lowering and resting.
(13) When the exercise routine is completed (assuming that the muscle has not become exhausted and caused automatic shutdown) discontinue the routine by turning off the computer.

While the method herein described and the form of apparatus for carrying this method into effect constitutes preferred embodiments of this invention, it is to be understood that the invention is not limited to this precise method and form of apparatus, and that changes may be made in either without departing from the scope of the invention which is defined in the appended claims.

What is claimed is:

1. Method of exercising a leg of a paralyzed person comprising the steps of:
   attaching a plurality of stimulation electrodes to said leg at locations for stimulating the quadriceps muscles thereof,
   seating said person in a chair,
   applying a series of stimulation signals to said electrodes to cause contraction of said quadriceps muscles and raising of said leg,
   applying a restraining force to said leg to cause increased muscular exertion during said raising,
   gradually increasing the stimulating effect of said stimulation signals to cause continued raising of said leg against said restraining force,
   after said leg has been raised a predetermined amount, gradually decreasing the stimulating effect of said stimulation signals to cause lowering of said leg to a rest position,
   resting said leg for a predetermined period of time, and
   repeating the above steps to produce an exercise routine.

2. Method according to claim 1 and further comprising the steps of:
   generating a profile signal representing a desired leg movement profile,
   generating a feedback signal representing actual movement achieved by said leg, and
   adjusting said stimulation signals in accordance with the difference between said profile signal and said feedback signal.

3. Apparatus for exercising a paralyzed leg comprising:
   a chair including a seat,
   a plurality of electrodes for stimulating controlled muscular activity in a paralyzed leg of a person seated in said chair,
   a profile generator for generating electrical representations of angles to be achieved by said leg at predetermined times during a desired raising and lowering sequence,
   stimulation means responsive to said profile generator for generating a series of stimulation signals corresponding to said electrical representations,
   connecting means for applying said stimulation signals to said electrodes so that said leg progresses through a raising and lowering sequence which achieves said angles at said predetermined times, and
   load means for applying a predetermined resisting force to said leg throughout said raising and lowering sequence.

4. Apparatus according to claim 3 and further comprising feedback means for generating electrical representation of leg angles actually achieved at predetermined times during a raising and lowering sequence produced as aforesaid, and computing means for causing said stimulation means to adjust said stimulation signals in accordance with differences between the electrical representations generated by said profile generator and said feedback means.

5. Apparatus according to claim 4 wherein said electrodes are transcutaneous electrodes.

6. Apparatus for exercising a paralyzed leg comprising:

a chair including a seat, load means for yieldably resisting lifting movement of a paralyzed leg of a person seated in said chair, a profile generator for generating a profile signal representing a desired lifting profile for said leg, feedback means for generating a feedback signal corresponding to actual lifting movement of said leg, and stimulation means responsive to said feedback signal and to said profile generator for stimulating normally paralyzed muscles within said leg to cause coordinated lifting movement thereof against the restraining action of said load means.

* * * * *

UNITED STATES PATENT AND TRADEMARK OFFICE
CERTIFICATE OF CORRECTION

PATENT NO. : 4,556,214

DATED : December 3, 1985

INVENTOR(S) : Jerrold S. Petrofsky et al.

It is certified that error appears in the above-identified patent and that said Letters Patent is hereby corrected as shown below:

Column 6, Ref. Numeral 122, "0 001 f" should be --0.001¼f--.

Column 7, line 19, Table III, delete "WSU 013A P2".

Column 7, Table III, line 32, "CS" should be --$\overline{CS}$--.

Column 7, Table III, line 33, "WR1" should be --$\overline{WR_1}$--.

Column 6, Table III, line 7, "Address" should be --Address bit 6--.

Column 6, Table III, line 10, "Write signal" should be --$\overline{Write\ signal}$--.

Column 8, line 32, "is", first occurrence, should be --in--.

Column 8, line 57, "members" should be --numbers--.

Column 18, line 48, "55016 should be --50016--.

Column 19, line 7, insert --into-- after "Z9" (second occurrence).

UNITED STATES PATENT AND TRADEMARK OFFICE
CERTIFICATE OF CORRECTION

PATENT NO. : 4,556,214

DATED : December 3, 1985

INVENTOR(S) : Jerrold S. Petrofsky et al.

It is certified that error appears in the above-identified patent and that said Letters Patent is hereby corrected as shown below:

Column 19, line 46, delete comma after "GO".

Signed and Sealed this

Fifteenth Day of April 1986

[SEAL]

Attest:

DONALD J. QUIGG

Attesting Officer

Commissioner of Patents and Trademarks